United States Patent [19]

Salvati et al.

[11] Patent Number: 4,526,892
[45] Date of Patent: Jul. 2, 1985

[54] DIMETHYLAMINOALKYL-3-(ERGOLINE-8'βCARBONYL)-UREAS

[75] Inventors: Patricia Salvati; Anna M. Caravaggi; Aldemio Temperilli; Germano Bosisio, all of Milan; Osvaldo Sapini, Gallarate; Enrico di Salle, Milan, all of Italy

[73] Assignee: Farmitalia Carlo Erba, S.p.A., Milan, Italy

[21] Appl. No.: 448,364

[22] Filed: Dec. 9, 1982

Related U.S. Application Data

[63] Continuation-in-part of Ser. No. 249,995, Mar. 3, 1981.

[51] Int. Cl.³ .................... C07D 457/06; A61K 31/48
[52] U.S. Cl. ........................................ 514/288; 546/69
[58] Field of Search ............................ 546/67, 68, 69; 424/261

[56]  References Cited

U.S. PATENT DOCUMENTS

| | | | |
|---|---|---|---|
| 3,245,996 | 4/1966 | Hoffmann et al. | 546/67 |
| 3,821,226 | 6/1974 | Fehr et al. | 546/67 |
| 3,904,634 | 9/1975 | Arari et al. | 424/261 |
| 4,176,182 | 11/1979 | Ferrari et al. | 424/261 |
| 4,180,581 | 12/1979 | Stadler et al. | 424/261 |
| 4,202,979 | 5/1980 | Kornfeld et al. | 424/261 |
| 4,219,556 | 8/1980 | Hauth et al. | 424/261 |

FOREIGN PATENT DOCUMENTS

| | | | |
|---|---|---|---|
| 274658 | 11/1962 | Australia | 424/261 |
| 738993 | 7/1966 | Canada | 546/69 |
| 3001752 | 7/1981 | Fed. Rep. of Germany | 546/69 |
| 615929 | 3/1980 | Switzerland | 546/67 |
| 634319 | 1/1983 | Switzerland | 546/67 |
| 811964 | 4/1959 | United Kingdom | 546/69 |

OTHER PUBLICATIONS

Bernardi, et al., "Derivati Della D.6–metil–8–β–aminometil–10α–ergoline", *Gazz Chem. Ital.* 94, 936–978 (1964).

*Primary Examiner*—Donald G. Daus
*Assistant Examiner*—G. Hendricks
*Attorney, Agent, or Firm*—Brooks Haidt Haffner & Delahunty

[57]  ABSTRACT

Novel ergoline derivatives formed by reaction of an 8-carboxy ergoline with a carbodiimide and having hypotensive and antiprolatinic activity.

4 Claims, No Drawings

DIMETHYLAMINOALKYL-3-(ERGOLINE-8'βCARBONYL)-UREAS

This application is a continuation-in-part of application Ser. No. 06/249,995 filed Mar. 3, 1981.

The invention relates to novel ergoline derivatives, to a process for their preparation and to therapeutic compositions containing them.

The invention provides ergoline derivatives having the general formula I

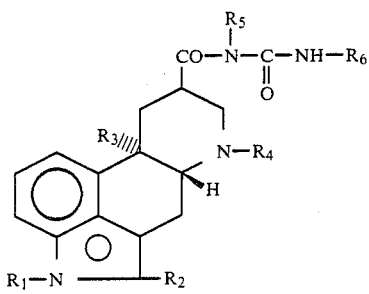

wherein $R_1$ represents a hydrogen atom or a methyl group; $R_2$ represents a hydrogen or halogen atom, a methyl or formyl group or a group of the formula S—$R_7$ or SO—$R_7$ wherein $R_7$ represents an alkyl group having from 1 to 4 carbon atoms or a phenyl group; $R_3$ represents a hydrogen atom or a methoxy group; $R_4$ represents a hydrocarbon group having from 1 to 4 carbon atoms, benzyl or phenthyl; and each of $R_5$ and $R_6$ independently represents an alkyl group having from 1 to 4 carbon atoms, a cyclohexyl group or a substituted or unsubstituted phenyl group or an acid and water-soluble group such as $(CH_2)_nN(CH_3)_2$ in which n is an integer, with the proviso that $R_5$ and $R_6$ cannot both be a said acid and water-soluble group, and the pharmaceutically acceptable addition salts with organic or inorganic acid thereof. In the general formula the term "halogen" should be construed to preferably encompass chlorine and bromine atom; nevertheless, term "halogen" also encompasses fluorine atom. In the definition of $R_5$ and $R_6$, n is preferably 1,2,3 and 4. In the definition of $R_4$, a hydrocarbon group having from 1 to 4 carbon atoms is intended to include alkyl, cycloalkyl and unsaturated (both ethylenically and acetylenically) groups.

Representative moieties include methyl, ethyl, n-propyl isopropyl, butyl, t-butyl, isobutyl, cyclopropyl, methylcyclopropyl, vinyl, allyl and propargyl.

The invention further provides a process for the preparation of ergoline derivatives of the general formula I as herein defined, which process comprises reacting an acid of the general formula II with a carbodiimide of the general formula III

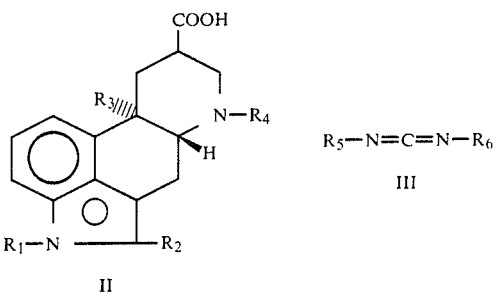

wherein $R_1$, $R_2$, $R_3$, $R_4$, $R_5$ and $R_6$ have the meanings given above.

The reaction is suitably carried out at a temperature of from 50°-100° C. for a period of from 5 to 24 hours in a solvent such as tetrahydrofuran, dimethylformamide or dioxan, optionally in the presence of an organic base such as pyridine or triethylamine. At the end of the reaction the products can be isolated and purified following conventional procedures, for example chromatography and/or crystallization. The intermediate acids having the general formula II are either known compounds or can be prepared from the corresponding esters by saponification. Formation of the desired pharmaceutically acceptable addition salts with organic and inorganic acids is carried out by known methods, e.g. reaction with an appropriate acid. The compounds according to the invention and their pharmaceutically acceptable salts are useful antihypertensive agents, and they also display from moderate to good antiprolactinic activity and from moderate to good activity against tumors, markedly prolactin dependent tumors.

EVALUATION OF ANTI-HYPERTENSIVE ACTIVITY

Four spontaneously hypertensive male rats, strain SHR, weighing 250–300 g for each group were used. The animals were treated once a day for four consecutive days. Drugs were administered by gastric gavage, suspended in 5% gum arabic (0.2 ml/100 g body weight) and blood pressure (BP) and heart rate (HR) were measured by indirected tail/cuff method (BP Recorder W+W). Blood pressure and heart rate were measured on the first and fourth days of treatment 1 hour before and 1 and 5 hours after drug administration. Hydralazine and α-methyl-Dopa were used as reference drugs. Results are reported in Tables 1 and 2.

EVALUATION OF THE TOXICITY

The male mice for each group were orally treated with drugs at different dose levels for the determination of orientative toxicity. Mice were observed for seven days after administration. The data obtained are summarized in Table 3.

TABLE 1

Changes in blood pressure (BP) in SHR rats. The values represent the mean obtained with 4 animals

| Compound of Example No. | Dose (mg/kg) os | 1st day | | 4th day | |
|---|---|---|---|---|---|
| | | Change in BP (Δ mmHg) | | | |
| | | 1 hour after dosing | 5 hours after dosing | 1 hour after dosing | 5 hours after dosing |
| 10 | 25 | −26 | −41 | −51 | −40 |
|    | 5  | −11 | −22 | −15 | −16 |
| 7  | 25 | −30 | −57 | −30 | −10 |
|    | 5  | −12 | −10 | −15 | −7  |

TABLE 1-continued

Changes in blood pressure (BP) in SHR rats. The values represent the mean obtained with 4 animals

| Compound of Example No. | Dose (mg/kg) os | 1st day | | 4th day | |
|---|---|---|---|---|---|
| | | Change in BP (Δ mmHg) | | | |
| | | 1 hour after dosing | 5 hours after dosing | 1 hour after dosing | 5 hours after dosing |
| 9 | 25 | −30 | −37 | −5 | −23 |
| 1 | 1 | −40 | −37 | −40 | −32 |
| | 0.5 | −27 | −20 | −20 | 0 |
| 12 | 10 | −26 | −37 | −71 | −28 |
| | 2 | −17 | −17 | −10 | −24 |
| 15 | 25.0 | −35 | −27 | −47 | −38 |
| 17 | 0.1 | −5 | −7 | −4 | −10 |
| | 1.0 | −20 | −19 | −43 | −66 |
| | 10.0 | −47 | −60 | −59 | −93 |
| 18 | 1.0 | −15 | −10 | −8 | −14 |
| | 12.5 | −19 | −19 | −38 | −47 |
| Hydralazine | 1 | −5 | −15 | −5 | 0 |
| | 5 | −40 | −20 | −20 | −7 |
| α-methyl-Dopa | 30 | −10 | −20 | −10 | 0 |
| | 100 | −10 | −25 | −20 | −25 |

TABLE 2

Changes in heart rate (HR) in SHR rats. The values represent the mean obtained with 4 animals.

| Compound of Example No. | dose (mg/kg) os | 1st day | | 4th day | |
|---|---|---|---|---|---|
| | | Change in HR (Δ beats/minute) | | | |
| | | 1 hour after dosing | 5 hours after dosing | 1 hour after dosing | 5 hours after dosing |
| 10 | 25 | −2 | −12 | −17 | −20 |
| | 5 | −5 | −20 | −20 | +15 |
| 7 | 25 | +5 | −20 | −17 | −2 |
| | 5 | 0 | −10 | 0 | 0 |
| 9 | 25 | −20 | −10 | 0 | −20 |
| 1 | 1 | −30 | −35 | −35 | −30 |
| | 0.5 | −20 | −12 | −20 | −7 |
| 12 | 10 | 0 | −30 | +17 | −10 |
| | 2 | −10 | −10 | −20 | −12 |
| 15 | 25 | −20 | −20 | −27 | −10 |
| 17 | 0.1 | −2 | +3 | −4 | −8 |
| | 1.0 | −20 | −23 | −27 | −22 |
| | 10.0 | +15 | −13 | −2 | +6 |
| 18 | 1.0 | −22 | −20 | +7 | −8 |
| | 12.5 | −10 | −15 | +2 | +5 |
| Hydralazine | 1 | +30 | +35 | +25 | +15 |
| | 5 | +40 | +45 | +18 | +15 |
| α-methyl-Dopa | 30 | +35 | +40 | +45 | +30 |
| | 100 | +70 | +40 | +50 | +10 |

TABLE 3

Acute Toxicity

| Compound of Example No. | Orientative toxicity in mice (mg/kg per os) |
|---|---|
| 10 | >800 |
| 7 | >800 |
| 9 | >800 |
| 1 | >250 <500 |
| 12 | >200 <400 |
| 15 | >800 |
| 17 | >100 <200 |
| 18 | >200 <400 |
| Hydralazine+ | 122 |
| α-methyl-Dopa+ | 5300 |

+ Data of $LD_{50}$ from the literature

RESULTS

Antihypertensive activity

Tables 1 and 2 report the results of the activity of the compounds under study on BP and HR in spontaneously hypertensive rats, SHR strain (4 rats each group).

With the compound of Example 10, 1,3-dicyclohexyl-3-(10′α-methoxy-1′,6′-dimethylergoline-8′β-carbonyl)-urea, at both the doses tried of 25 and 5 mg/kg a decrease of BP was observed; this effect was long lasting because it was still marked on the fourth day at both the first and fifth hour after dosing.

The compound of Example No. 7, 1,3-dicyclohexyl-3-(6′-methylergoline-8′β-carbonyl)-urea, was tried at the doses of 25 and 5 mg/kg; a significant decrease BP was observed with the higher dose used both on the first and fourth days of treatment; with the dose of 5 mg/kg the antihypertensive effect was less remarkable.

The compound of Example No. 9, 1,3-dicyclohexyl-3-(10′α-methylergoline-8′β-carbonyl)-urea, at the dose of 25 mg/kg produced a marked decrease of BP on the first day of treatment; the hypotensive effect was still observed on the fourth day even if less remarkable at the first hour after dosing.

The compound of Example No. 1, 1,3-diisopropyl-3-(6′-methylergoline-8′β-carbonyl)-urea, was tried at the doses of 1 and 0.5 mg/kg and it produced a marked decrease of BP in a dose dependent manner.

The compound of Example No. 12, 1,3-di-t-butyl-3-(10′α-methoxy-6′-methylergoline-8′βcarbonyl)-urea, tested at the doses of 10 and 2 mg/kg also reduced BP in a dose dependent manner; the greatest hypotensive effect was observed on the fourth day, one hour after the administration of 10 mg/kg.

All the compounds tested produced only a moderate bradycardia. The compound of Example No. 15, 1,3-dicyclohexyl-3-(6′-allylergoline-8′β-carbonyl)-urea, was administered at the dose of 25 mg/kg b.w. and produced a decrease in BP both on the 1st and 4th days of treatment but more pronounced on the 4th day. This was a long lasting activity and was still at its peak 5 hours after administration.

The dose response curve was determined in order to evaluate the hypotensive activity of the compound of Example No. 17, 1,3-di-t-butyl-3-(10′α-methoxy-1′,6′-dimethylergoline-8′β-carbonyl)-urea. The tried doses were 10, 1 and 0.1 mg/kg b.w. The hypotensive effect was dose related as well as very marked with the highest dose tried (10 mg/kg b.w.) on both the 1st and 4th day of treatment. No effect was obtained with the lowest dose (0.1 mg/kg b.w.)

The compound of Example No. 18, 1,3-di-t-butyl-3-(1′,6′-dimethylergoline-8′β-carbonyl)-urea, reduced BP with both the tested doses (12.5 and 1 mg/kg b.w.); this effect was dose dependent. The hypotensive activity observed with the highest dose was very remarkable on the 4th day of treatment and still lasting 5 hours after administration.

COMPARISON WITH REFERENCE DRUGS

Compounds 1,3-dicyclohexyl-3-(10′α-methoxy-1′,6′-dimethylergoline-8′β-carbonyl)-urea (Example No. 10), 1,3-dicyclohexyl-3-(6′-methylergoline-8′β-carbonyl)-urea (Example No. 7) and 1,3-dicyclohexyl-3 (10′α-methoxy-6′-methylergoline-8′β-carbonyl)-urea (Example No. 9) at the dose of 25 mg/kg have a hypotensive activity comparable to that of Hydralazine at the dose of 5 mg/kg, but show no tolerance on the 4th day, unlike Hydralazine.

The compound, 1,3-diisopropyl-3-(6'-methylergoline-8'β-carbonyl)-urea (Example No. 1) shows a greater and longer lasting hypotensive activity than Hydralazine. The compound 1,3-di-t-butyl-3-(10'αmethoxy-6'-methylergoline-8'β-carbonyl)-urea (Example No. 12) at the dose of 10 mg/kg shows comparable activity to that of Hydralazine at the dose of 5 mg/kg on the 1st day, but a greater activity on the 4th day because tolerance does not occur.

The hypotensive activity of compounds 1,3-dicyclohexyl-3-(6'-allylergoline-8'β-carbonyl)-urea (25 mg/kh b.w.) (Example No. 15), 1,3-di-t-butyl-3(10'α-methoxy-1',6'-dimethoxyergoline-8'β-carbonyl)-urea (1 mg/kg b.w.) (Example No. 17) and 1,3-di-t-butyl-3-(1',6'-dimethylergoline-8'β-carbonyl)urea (12.5 mg/kg b.w.) (Example No. 18) was comparable to that of Hydralazine (5 mg/kg b.w.) on the first day of treatment, but was much more remarkable on the 4th day.

The compound 1,3-di-t-butyl-3-(10'α-methoxy-1',6'-dimethoxyergoline-8'βcarbonyl)-urea at its higher dose (10 mg/kg b.w.) (Example No. 17) also produced an hypotensive effect larger than Hydralazine on both the 1st and 4th days of treatment.

Compared with α-methyl-Dopa tested at the dose of 30 and 100 mg/kg the tested compounds according to the invention all show a greater hypotensive effect. Considering the activity on HR, the tested compounds according to the invention do not produce any increase of HR as Hydralazine and α-methyl-Dopa do, but, on the contrary, a moderate bradycardia is observed.

TOXICITY

Finally the toxicity of the compounds according to the invention, expressed as orientative toxicity in mice (Table 3) is not greater than Hydralazine and is lower in some cases. The tested compounds according to the invention also have a better therapeutic index than α-methyl-Dopa.

EVALUATION OF ANTI-PROLACTIN ACTIVITY

The compounds of this invention have proved to possess a strong anti-prolactin activity in rats and a low emetic activity in dogs. The prolactin secretion inhibitory action of the compounds has been indirectly evaluated by determining the egg-nidation inhibitory action in rats. For the ergoline derivatives this activity is considered to be correlated with the anti-prolactin activity (E. FLUCKIGER and E. DEL POZO,Handb. exp. Pharmac. 49, 615, 1978), since prolactin is the only hypophysial hormone involved in the maintenance of the first part of pregnancy in rats (W. K. MORISHIGE and I. ROTHCHILD, Endocrinology 95, 260, 1974).

Pregnant Sprague Dawley rats weighing 200–250 g were used. The compounds to be tested, dissolved in diluted mineral acids, were administered orally to groups from six to eight rats on day 5 of pregnancy. The animals were sacrificed on day 14 and the uteri were examined. The absence of implantation sites was taken as the criterion of anti-prolactin activity. Several doses were tested for the $ED_{50}$ evaluation. As reference standard Bromocriptine was used.

The emetic activity of the compounds was investigated by oral administration to male beagle dogs weighing 15–20 kg. The animals were observed for 6 hours after the treatment. Four to six animals per dose were employed for the $ED_{50}$ evaluation. The results obtained are reported in TABLE 4. From Table 4 it appears that the new ergoline derivatives are 19 to 285 times more active than Bromocriptine as nidation inhibitors. The emetic activity of the compounds is similar or lower than that of Bromocriptine. The ratio between activity and tolerance of the new ergoline derivatives accordingly is very high.

From the above results it can be seen that the new derivatives may find an advantageous clinical exploitation in all the situations in which it is desirable to reduce prolactin levels such as inhibition of puerperal lactation, inhibition of galactorrhoea and treatment of infertility due to hyperprolactinaemia. The compounds, of the present invention may also find utility, like bromocriptine, for the treatment of Parkinson's disease and acromegaly.

TABLE 4

| Name of Compound | Nidation Inhibition in Rats ≃$ED_{50}$ mg/kg p.o. | Emetic activity in Dogs ≃$ED_{50}$ mg/kg p.o. |
| --- | --- | --- |
| 1,3-diisopropyl-3-(6'-n-propylergoline-8'β-carbonyl)-urea (Example No. 5) | 0.02 | 0.01 |
| 1-ethyl-3-(3'-dimethylaminopropyl)-3-(6'-methylerogoline-8'β-carbonyl)-urea (Example No. 13) | 0.3 | 0.01 |
| 1-ethyl-3-(3'-dimethylaminopropyl)-3-(6'-allylergoline-8'β-carbonyl)-urea (Example No. 19) | 0.03 | 0.02 |
| 1-(3'-dimethylaminopropyl)-3-ethyl-3-(6'-allylergoline-8'β-carbonyl)-urea (Example No. 20) | 0.27 | — |
| 1-ethyl-3-(3'dimethylaminopropyl)-3-(6'-n-propylergoline-8'β-carbonyl)-urea (Example No. 21) | 0.02 | 0.02–0.04 |
| 1,3-dimethyl-3-(6'-allylergoline-8'β-carbonyl)-urea (Example No. 24) | 0.5 | — |
| 2-bromo-α-ergocryptine | 5.7 | 0.01–0.02 |

The following Examples illustrate preparation of some compounds of the present invention, without limiting it.

EXAMPLE 1

1,3-diisopropyl-3-(6'-methylergoline-8'β-carbonyl)urea (I: $R_1=R_2=R_3=H$, $R_4=CH_3, R_5=R_6=(CH_3)_2CH$)

A mixture of 5 g of 6-methyl-8β-carboxy-ergoline and 2.3 g of diisopropyl carbodiimide in 500 ml of tetrahydrofuran were refluxed, with stirring and under nitrogen, for 24 hours. The resultant solution was evaporated in vacuo to dryness and the residue taken up with chloroform and 5% sodium hydroxide solution. The organic phase was separated, dried over anhydrous sodium sulphate and evaporated in vacuo. The residue was chromatographed on silica (eluant chloroform with 1% methanol) to give 5.8 g of the title compound, m.p. 202°–204° C., after crystallization from diethyl ether.

EXAMPLE 2

1,3-diisopropyl-3-(1',6'-dimethylergoline-8'β-carbonyl)urea (I: $R_1=R_4=CH_3$, $R_2=R_3=H$, $R_5=R_6=(CH_3)_2CH$)

Operating as in Example 1, but employing 1,6-dimethyl-8β-carboxy-ergoline in place of 6-methyl-8βcarboxy-ergoline, the title compound, m.p. 172°–174° C., was obtained in 75% yield.

EXAMPLE 3

1,3-diisopropyl-3-(10'α-methoxy-6'-methylergoline-8'β-carbonyl)urea (I: $R_1=R_2=H$, $R_3=CH_3O$, $R_4=CH_3$, $R_5=R_6=(CH_3)_2CH$)

Operating as in Example 1, but employing 10α-methoxy-6-methyl-8β-carboxy-ergoline in place of 6-methyl-8β-carboxy-ergoline, the title compound, m.p. 190°–192° C., was obtained in 79% yield.

EXAMPLE 4

1,3-diisopropyl-3-(10'α-methoxy-1',6'-dimethylergoline-8'βcarbonyl)urea (I: $R_1=R_4=CH_3$, $R_2=H$, $R_3=CH_3O$, $R_5=R_6=(CH_3)_2CH$)

Operating as in Example 1, but employing 10α-methoxy-1,6-dimethyl-8β-carboxy-ergoline in place of 6-methyl-8β-carboxy-ergoline, the title compound, m.p. 180°–182° C., was obtained in 80% yield.

EXAMPLE 5

1,3-diisopropyl-3-(6'-n-propylergoline-8'β-carbonyl)-urea (I: $R_1=R_2=R_3=H$, $R_4=CH_3CH_2CH_2$, $R_5=R_6=(CH_3)_2CH$)

Operating as in Example 1, but employing 6-n-propyl-8β-carboxy-ergoline in place of 6-methyl-8βcarboxy-ergoline, the title compound, m.p. 188°–190° C., was obtained in 82% yield.

EXAMPLE 6

1,3-diisopropyl-3-(2',6'-dimethylergoline-8'β-carbonyl)-urea (I: $R_1=R_3=H$, $R_2=R_4=CH_3$, $R_5=R_6=(CH_3)_2CH$)

Operating as in Example 1, but employing 2,6-dimethyl-8β-carboxy-ergoline in place of 6-methyl-8β-carboxy-ergoline, the title compound, m.p. 192°–194° C., was obtained in 85% yield.

EXAMPLE 7

1,3-dicyclohexyl-3-(6'-methylergoline-8'β-carbonyl)urea (I: $R_1=R_2=R_3=H$, $R_4=CH_3$, $R_5=R_6=$cyclohexyl)

Operating as in Example 1, but employing dicyclohexyl carbodiimide in place of diisopropyl carbodiimide, the title compound, m.p. 205°–207° C., was obtained in 77% yield.

EXAMPLE 8

1,3-dicyclohexyl-3-(1',6'-dimethylergoline-8'βcarbonyl)-urea (I: $R_1=R_4=CH_3$, $R_2=R_3=H$, $R_5=R_6=$cyclohexyl)

Operating as in Example 2, but employing dicyclohexyl carbodiimide in place of diisopropyl carbodiimide, the title compound, m.p. 182°–184° C., was obtained in 83% yield.

EXAMPLE 9

1,3-dicyclohexyl-3-(10'α-methoxy-6'-methylergoline-8'β-carbonyl)-urea (I: $R_1=R_2=H$, $R_3=CH_3O$, $R_4=CH_3$, $R_5=R_6=$cyclohexyl)

Operating as in Example 3, but employing dicyclohexyl carbodiimide in place of diisopropyl carbodiimide, the title compound m.p. 229°–231° C., was obtained in 75% yield.

EXAMPLE 10

1,3-dicyclohexyl-3-(10'α-methoxy-1',6'-dimethylergoline-8'β-carbonyl)-urea (I: $R_1=R_4=CH_3$, $R_2=H$, $R_3=CH_3O$, $R_5=R_6=$cyclohexyl)

Operating as in Example 4, but employing dicyclohexyl carbodiimide in place of diisopropyl carbodiimide, the title compound, m.p. 198°–200° C., was obtained in 80% yield.

EXAMPLE 11

1,3-di-tert-butyl-3-(6'-methylergoline-8'β-carbonyl)-urea (I: $R_1=R_2=R_3=H$, $R_4=CH_3$, $R_5=R_6=(CH_3)_3C$)

Operating as in Example 1, but employing di-t-butyl carbodiimide in place of diisopropyl carbodiimide, the title compound, m.p. 194°–196° C., was obtained in 75% yield.

EXAMPLE 12

1,3-di-t-butyl-3-(10'αmethoxy-6'-methylergoline-8'β-carbonyl)-urea (I: $R_1=R_2=H$, $R_3=CH_3O$, $R_4=CH_3$, $R_5=R_6=(CH_3)_3C$)

Operating as in Example 3, but employing di-t-butyl carbodiimide in place of diisopropyl carbodiimide, the title compound, m.p. 138°–140° C., was obtained in 65% yield.

EXAMPLE 13

1-ethyl-3-(3'-dimethylaminopropyl)-3(6'-methylergoline-8'β-carbonyl)-urea (I: $R_1=R_2=R_3=H$, $R_4=CH_3$, $R_5=(CH_3)_2-NCH_2CH_2CH_2$, $R_6=C_2H_5$)

Operating as in Example 1, but employing N-(3-dimethylaminopropyl)—N-ethyl carbodiimide in place of diisopropyl carbodiimide, the title compound, m.p. 179°–181° C., was obtained in 75% yield.

EXAMPLE 14

1-ethyl-3-(3'-dimethylaminopropyl)-3-(10'α-methoxy-6'-methylergoline-8'β-carbonyl)urea (I: $R_1=R_2=H$, $R_3=CH_3O$, $R_4=CH_3$, $R_5=(CH_3)_2NCH_2CH_2CH_2$, $R_6=C_2H_5$)

Operating as in Example 3, but employing N-(3-dimethylaminopropyl)-N'-ethyl carbodiimide in place of diisopropyl carbodiimide, the title compound m.p. 169°–171° C. was obtained in 78% yield.

EXAMPLE 15

1,3-dicyclohexyl-3-(6'-allylergoline-8'β-carbonyl)-urea (I: $R_1=R_2=R_3=H$, $R_4=CH_2=CH—CH_2$, $R_5=R_6=$cyclohexyl)

Operating as in Example 7, but employing 6-allyl-8β-carboxy-ergoline in place of 6-methyl-8β-carboxy-ergoline, the title compound, m.p. 152°–154° C., was obtained in 80% yield.

EXAMPLE 16

1,3-dimethyl-3-(6'-methylergoline-8'β-carbonyl)urea (I: $R_1=R_2=R_3=H$, $R_4=R_5=R_6=CH_3$)

Operating as in Example 1, but employing dimethyl carbodiimide in place of diisopropyl carbodiimide, the title compound, m.p. 215°–217° C. was obtained in 74% yield.

EXAMPLE 17

1,3-di-tert-butyl-3-(10'α-methoxy-1',6'-dimethylergoline-8'β)-carbonyl)-urea (I: $R_1=R_4=CH_3$, $R_2=H$, $R_3=CH_3O$, $R_5=R_6=(CH_3)_3C$)

Operating as in Example 4, but employing di-t-butyl carbodiimide in place of diisopropyl carbodiimide, the title compound, m.p. 140°–142° C. was obtained in 60% yield.

EXAMPLE 18

1,3-di-tert-butyl-3-(1',6'-dimethylergoline-8'β-carbonyl)urea (I: $R_1=R_4=CH_3$, $R_2=R_3=H$, $R_5=R_6=(CH_3)_3C$)

Operating as in Example 2, but employing di-t-butyl carbodiimide in place of diisopropyl carbodiimide, the title compound, m.p. 180°–181° C., was obtained in 65% yield.

EXAMPLE 19

1-ethyl-3-(3'-dimethylaminopropyl)-3-(6'-allylergoline-8'βcarbonyl)-urea (I: $R_1=R_2=R_3=H$, $R_4=CH_2=CH-CH_2$, $R_5=(CH_3)_2-NCH_2CH_2CH_2$, $R_6=C_2H_5$)

Operating as in Example 13, but employing 6-allyl-8'β-carboxy-ergoline in place of 6-methyl-8β-carboxy-ergoline, the title compound was obtained in 60% yield as diphosphate salt m.p. 153°–155° C.

EXAMPLE 20

1-(3'-dimethylaminopropyl)-3-ethyl-3-(6'-allylergoline-8'β-carbonyl)-urea (I: $R_1=R_2=R_3=H$, $R_4=CH_2=CH-CH_2$, $R_5=C_2H_5$, $R_6=(CH_3)_2NCH_2CH_2CH_2$)

Operating as in Example 19, after separation of 1-ethyl-3-(3'-dimethylaminopropyl)-3-(6'-allylergoline-8'β-carbonyl)-urea, the mother-liquor was chromatographed on silica gel using $CHCl_3/1$–2% MeOH as eluant to give the title compound in 30% yield as diphosphate salt, m.p. 149°–151° C.

EXAMPLE 21

1-ethyl-3-(3'-dimethylaminopropyl)-3-(6'-n-propylergoline-8'β-carbonyl)-urea (I: $R_1=R_2=R_3=H$, $R_4=CH_3CH_2CH_2$, $R_5=(CH_3)_2NCH_2-CH_2CH_2$, $R_6=C_2H_5$)

Operating as in Example 13, but employing 6-n-propyl-8β-carboxy-ergoline in place of 6-methyl-8β-carboxy-ergoline, the title compound was obtained in 70% yield as dichloride salt, m.p. 205°–207° C.

EXAMPLE 22

1-ethyl-3-(3'-dimethylaminopropyl)-3-(6'-isopropylergoline-8'β-carbonyl)-urea (I: $R_1=R_2=R_3=H$, $R_4=(CH_3)_2CH$, $R_5=(CH_3)_2NCH_2-CH_2CH_2$, $R_6=C_2H_5$)

Operating as in Example 13, but employing 6-isopropyl-8β-carboxy-ergoline, the title compound, m.p. 106°–108° C., was obtained in 55% yield.

EXAMPLE 23

1,3-dicyclohexyl-3-(1'-methyl-6'-allylergoline-8'β-carbonyl)-urea (I: $R_1=CH_3$, $R_2=R_3=H$, $R_4=CH_2CH=CH_2$, $R_5=R_6=$cyclohexyl)

Operating as in Example 7, but employing 1-methyl-6-allyl-8β-carboxy-ergoline in place of 6-methyl-8β-carboxy-ergoline, the title compound, m.p. 137°–139° C., was obtained in 75% yield.

EXAMPLE 24

1,3-Dimethyl-3-(6'-allylergoline-8'β-carbonyl)-urea (I: $R_1=R_2=R_3=H$, $R_4=CH_2=CH-CH_2$, $R_5=R_6=CH_3$)

Operating as in Example 15, but employing dimethylcarbodiimide in place of dicyclohexylcarbodiimide, the title compound, m.p. 106°–108° C., was obtained in 67% yield.

What we claim is:

1. Compounds of formula

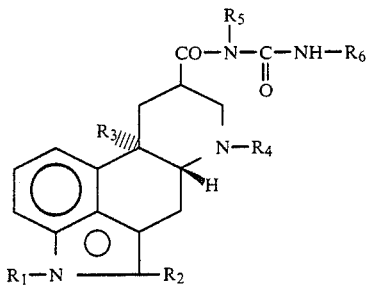

wherein $R_1$ is a hydrogen atom or a methyl group; $R_2$ is a hydrogen atom; $R_3$ is a hydrogen atom or a methoxy group; $R_4$ is an alkyl or an alkenyl group selected from methyl, allyl and propyl groups; and each of $R_5$ and $R_6$ independently is an alkyl group having from 1 to 3 carbon atoms or a group of the formula $(CH_2)_nN(CH_3)_2$ in which n is 3 with the proviso that at least one of $R_5$ and $R_6$ is said dimethylaminoalkyl group, and pharmaceutically acceptable addition salts with organic or inorganic acid thereof.

2. A compound according to claim 1 which is selected from the group consisting of:
1-ethyl-3-(3'-dimethylaminopropyl)-3(6'-methylergoline-8'β-carbonyl)-urea;
1-ethyl-3-(3'-dimethylaminopropyl)-3-(10'α-methoxy-6'-methylergoline-8'β-carbonyl)-urea;
1-(3'-dimethylaminopropyl)-3-ethyl-3-(6'-allylergoline-8'β-carbonyl)-urea; and
1-ethyl-3-(3'-dimethylaminopropyl)-3-(6'-n-propylergoline-8'β-carbonyl)-urea.

3. A pharmaceutical composition containing a therapeutically effective amount of a compound according to claim 1, in admixture with a pharmaceutically acceptable carrier for oral or parenteral administration.

4. 1-ethyl-3-(3'dimethylaminopropyl)-3-(6'-allylergoline-8'β-carbonyl)-urea.

* * * * *